(12) United States Patent
Ahlers et al.

(10) Patent No.: US 8,216,602 B2
(45) Date of Patent: Jul. 10, 2012

(54) NERVE GUIDE

(75) Inventors: Michael Ahlers, Eberbach (DE); Burkhard Schlosshauer, Tuebingen (DE); Lars Dreesmann, Kusterdingen (DE); Martin Lietz, Kusterdingen-Immenhausen (DE)

(73) Assignee: Gelita AG, Eberbach (DE)

( * ) Notice: Subject to any disclaimer, the term of this patent is extended or adjusted under 35 U.S.C. 154(b) by 1002 days.

(21) Appl. No.: 12/120,296

(22) Filed: May 14, 2008

(65) Prior Publication Data

US 2009/0024150 A1 Jan. 22, 2009

Related U.S. Application Data

(63) Continuation of application No. PCT/EP2006/010976, filed on Nov. 16, 2006.

(30) Foreign Application Priority Data

Nov. 17, 2005 (DE) .................. 10 2005 054 941

(51) Int. Cl.
*A61F 2/00* (2006.01)
(52) U.S. Cl. .......................... 424/426; 514/2; 623/1.38
(58) Field of Classification Search .................. None
See application file for complete search history.

(56) References Cited

U.S. PATENT DOCUMENTS

| | | | |
|---|---|---|---|
| 4,863,668 A | 9/1989 | Griffiths et al. | |
| 4,963,146 A | 10/1990 | Li | |
| 5,879,359 A | 3/1999 | Dorigatti et al. | |
| 6,855,860 B2 | 2/2005 | Ruszczak et al. | |
| 7,084,082 B1 | 8/2006 | Shimizu | |
| 2003/0195618 A1 | 10/2003 | Abraham et al. | |
| 2004/0073155 A1 | 4/2004 | Laufer et al. | |
| 2006/0018947 A1 | 1/2006 | Mueller et al. | |
| 2007/0077274 A1 | 4/2007 | Ahlers | |

FOREIGN PATENT DOCUMENTS

| | | |
|---|---|---|
| DE | 693 28 100 | 12/2000 |
| DE | 100 53 611 | 5/2002 |
| DE | 101 29 871 | 10/2002 |
| DE | 10 2004 024 635 | 12/2005 |
| EP | 0 306 187 | 3/1989 |
| EP | 0 327 022 | 8/1989 |
| EP | 0 608 139 | 7/1994 |
| EP | 0 945 145 | 9/1999 |
| EP | 0 982 038 | 3/2000 |
| EP | 1 084 686 | 3/2001 |
| EP | 1 112 047 | 7/2001 |
| EP | 1 201 202 | 5/2002 |
| EP | 1 201 256 | 5/2002 |
| EP | 1 254 671 | 11/2002 |
| EP | 1 263 485 | 12/2002 |
| EP | 1 586 285 | 10/2005 |
| GB | 2 366 736 | 3/2002 |
| WO | WO 89/10728 | 11/1989 |
| WO | WO 94/03212 | 2/1994 |
| WO | WO 95/20359 | 8/1995 |
| WO | WO 97/37002 | 10/1997 |
| WO | WO 98/10728 | 3/1998 |
| WO | WO 98/28364 | 7/1998 |
| WO | WO 01/66162 | 9/2001 |
| WO | WO 03/086290 | 10/2003 |
| WO | WO 2004/071736 | 8/2004 |
| WO | WO 2005/042043 | 5/2005 |
| WO | WO 2005/111121 | 11/2005 |

OTHER PUBLICATIONS

Borges, J. et al., *Der Chirurg*, 75:284-290 (2004).
Chen, Yeuh-Sheng et al., *Biomaterials*, 26(18):3911-3918 (2005).
Cheng, M. et al., *Biomaterials*, 24:2871-2880 (2003).
Gámez, E. et al., *Cell Transplantation*, 12:481-490 (2003).
Gámez, E. et al., *Cell Transplantation*, 13:549-564 (2004).
Liu, Bai-Shuan et al., *Journal of Biomaterials Applications*, 19:21-34 (2004).
Schlosshauer, B. et al., Nerve Guides, *Encyclopedia of Biomaterials and Biomedical Engineering*, pp. 1043-1053 (2004).
International Search Report for PCT/EP2006/010976 filed Nov. 16, 2005.

*Primary Examiner* — Anand Desai
(74) *Attorney, Agent, or Firm* — Leydig, Voit & Mayer, Ltd.

(57) ABSTRACT

The aim of the invention is to provide a nerve guide that allows the axons to develop fairly freely during regeneration. For this purpose, the nerve guide is produced based on a shaped body from a cross-linked, resorbable, gelatin-based material. The shaped body is a tubular hollow body having a wall with an exterior surface and an interior surface, which wall defines a lumen. The nerve guide comprises a semipermeable layer surrounding the lumen.

44 Claims, 8 Drawing Sheets

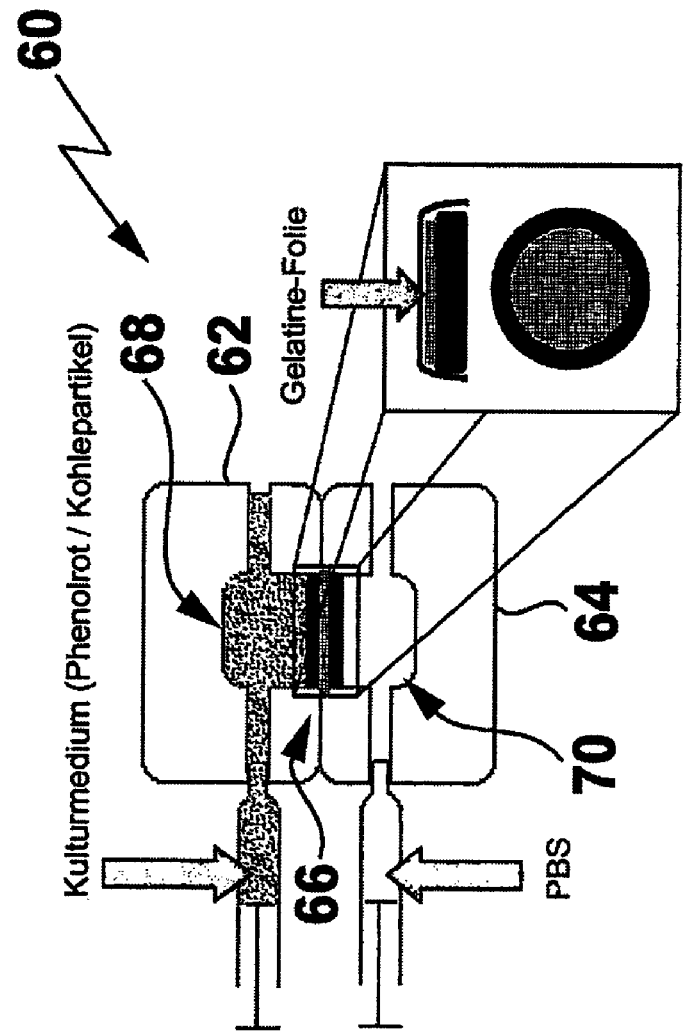

Diffusion (Phenolrot)     FIG.6
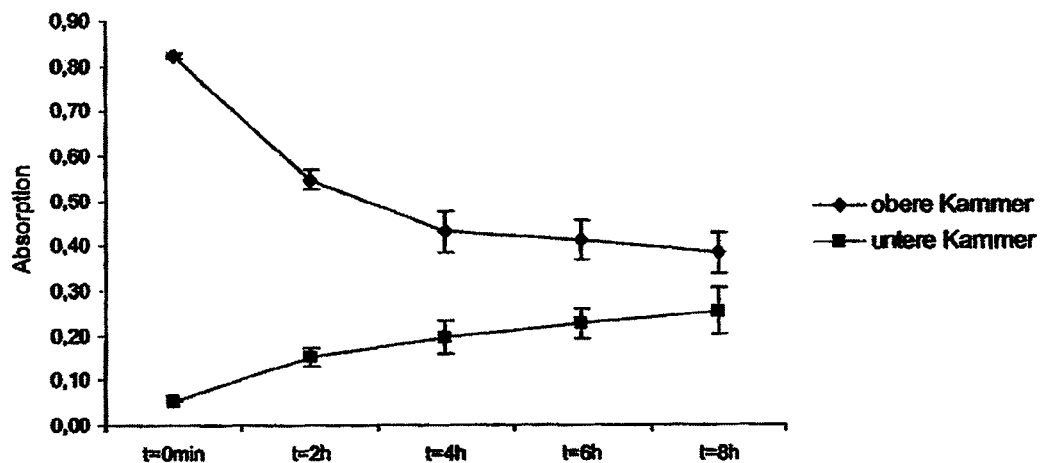
Diffusion (Phenolrot)     FIG.7
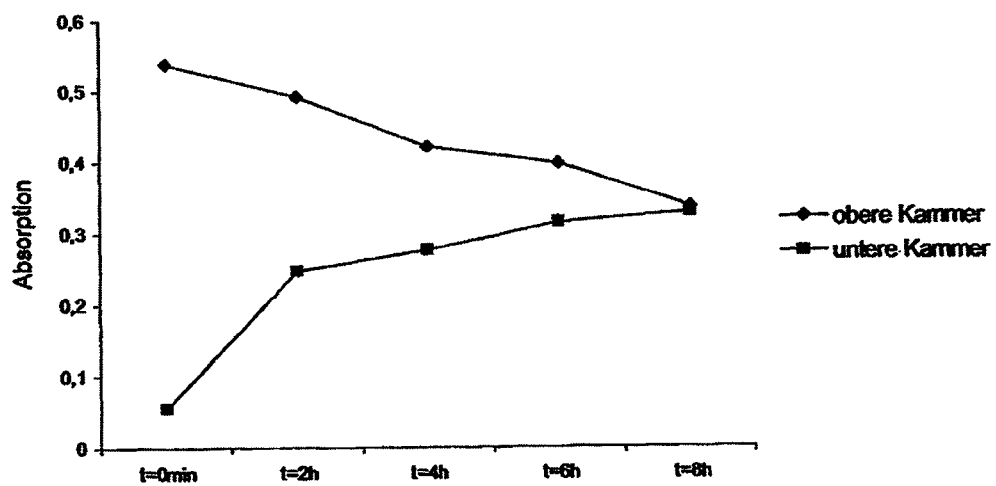

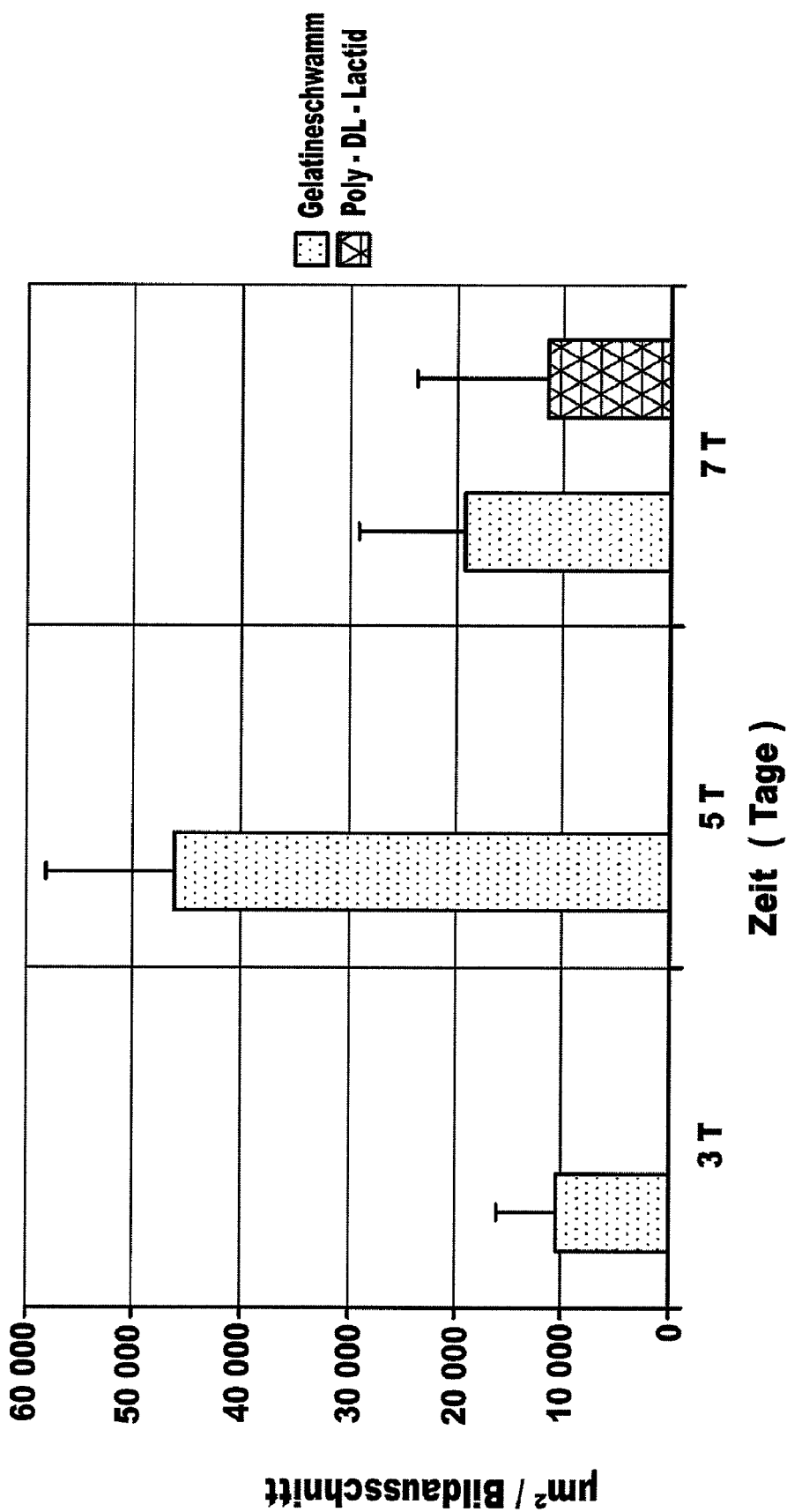

NERVE GUIDE

CROSS-REFERENCE TO RELATED APPLICATIONS

This patent application is a continuation of PCT Application No. PCT/EP2006/010976, filed Nov. 16, 2006, which claims priority of German patent Application No. 10 2005 054 941.1, filed Nov. 17, 2005, which are each incorporated by reference.

BACKGROUND OF THE INVENTION

The present invention relates to a nerve guide comprising a shaped body made from a resorbable material.

Nerve guides of the kind described at the beginning are used for lesions of the nervous system in order to link the ends of damaged nerves and to bridge the gap between the two ends. In this way, the nerve guide provides the nerve fibers (axons) space to grow and ideally also provides protection against penetration by scar-forming, connective tissue cells (fibroblasts).

The two ends of the nerve guide then receive the two nerve stumps formed at the lesion and bridge the gap existing between them. The lumen of the nerve guide remaining between the nerve stumps specifies the direction for the regenerating axons and avoids any incorrectly-guided growth of these, a targeted regeneration being thereby promoted.

Biologically degradable or resorbable nerve guides are preferred for this as compared with non-resorbable, since after the nerve fibers have been restored or during this, the nerve guide breaks down and accordingly, in contrast to non-resorbable nerve guides, a further operation to remove the same is avoided, such an operation being necessary in some circumstances and itself in turn bringing the risk of damage to the nerve fibers. However, the stability of the resorbable nerve guide must be adjustable in respect of resorption mechanisms, which presents a challenge.

An object of nerve regeneration by means of nerve guides is restoration of motor and sensory functions as well as preventing incorrect guiding of nerve growth and formation of painful neuromas.

Regenerative medicine can up until now offer only unsatisfactory therapies for damage to nerve fibers of the nervous system. Although most adult neurones in principle have the capability of regenerating axons, only limited functional regeneration is found in the peripheral nervous system in the absence of assistance and as good as none at all in the central nervous system.

Reasons for these limitations are inter alia the loss of contact with the original nerve pathway and the formation of inhibiting scars.

An operative bridging of lesioned/inhibitory areas represents in principle a successful strategy for therapy, for which in practice however up to now autologous nerve transplants (mostly the sural nerve of the lower leg) were almost exclusively used.

The disadvantages connected with this such as morbidity in the donor region and limited availability have substantially stimulated development of synthetic nerve guides. Nerve guides in the form of hollow tubes have in more recent times been developed, made from different inert and resorbable, pure synthetic polymers and biological constituents, such as for example polysaccharides, collagen or specific cross-linked gelatin materials.

BRIEF SUMMARY OF THE INVENTION

It is an object of the present invention to further improve the nerve guide of the kind described at the beginning, in order to facilitate development of axons during regeneration in a manner which is as far as possible unhindered.

This object is met according to the invention, by the nerve guides of the kind described at the beginning comprising a shaped body made from a cross-linked, resorbable, gelatin-based material, the shaped body being a hollow body in the form of a tubule and having a wall with an external surface and an internal surface which defines a lumen, and the nerve guide comprising a semipermeable layer surrounding the lumen.

Readily sterilizable nerve guides can be formed as implants from materials based on gelatin, which can be stored even for a long period of time, in particular also at room temperature. Also, nerve guides of this kind can be adapted, even in the operating theatre, as to their length and also in respect of other requirements.

Materials based on gelatin may also be prepared in a defined way and reproducibly in their composition and in their resorption properties. Also, materials of this kind prove to be calculable in respect of their (patho)physiological reactions. Furthermore, the materials generally have the required biocompatibility and are neither toxic, infectious nor inflammatory.

Moreover, materials based on gelatin are also suitable in order to produce nerve guides which meet the mechanical requirements of an implant. At the same time, the materials can be so formulated that that they exhibit sufficient flexibility during handling by a surgeon in the course of an operation as well as post-operatively as an inserted implant, so that compression of the nerves is avoided and adaptation to movements of the body parts of the patient treated is possible.

On the other hand, sufficient shape stability can be assured by the materials based on gelatin used according to the invention for the shaped body, this avoiding collapse of the inserted implant.

Furthermore, sufficiently strong nerve guides can be produced to facilitate stitching of the implant at the nerve stumps formed at the lesion.

DETAILED DESCRIPTION OF THE INVENTION

According to the present invention, a layer of the nerve guide which can form part of the shaped body, is formed to be semipermeable. This means that diffusion of nutrient and gas between the lumen and the environs of the nerve guide is feasible in the radial direction, in a manner which is as far as possible unhindered, while on the other hand, diffusion of unwanted substances from the surrounding tissue is prevented, in particular penetration of cells, such as for example fibroblasts.

For realisation of this protective function of the semipermeable layer, different possibilities are available, which in part may also be combined with one another.

Thus the semipermeable layer of the nerve guide may have, for example, pores which are on average less than about 0.5 µm. Cells cannot pass through so-called nanopores of this kind, while on the other hand, diffusion of nutrient and gas through pores of this kind can take place almost unhindered.

As an alternative to this, a gel structure may be used, which on the one hand facilitates diffusion of nutrient and gas as above, and one the other hand acts as a cell barrier.

In another embodiment, the nerve guide has, as semipermeable layer, a barrier layer, which is substantially impermeable for positively laden species, in particular cells, especially fibroblasts, since cells often carry positive loadings on their surface and therefore adhere poorly to positively laden surfaces.

Another embodiment has a semipermeable layer which is extremely hydrophilic, and here it is also observed that cell diffusion is greatly hindered by a layer of this kind.

A similar effect may also be achieved by a layer which is hydrophobic. Here also cell migration is markedly reduced.

Hydrophobic layers may for example be formed from a material which comprises gelatin modified with esters of fatty acids. An example of this is dodecenyl succinated gelatin.

Preferably, for materials of this kind, the gelatin is modified at the amino groups of the lysine groups, in particular at 10 to 80% of the lysine groups, with esters of fatty acids.

Finally, as a further variant, the nerve guide or its shaped body has immobilised repulsion proteins, for example semaphorins, on the external surface as semipermeable layer, these inhibiting inward migration of cells.

The mechanical strength of the nerve guides according to the invention, as already discussed further above, must, in application, i.e. during use as an implant, permit stitching. The strength needed for this, in particular also tear-out strength relative to the stitching materials used, can be achieved in particular by use of reinforcing materials, which are in particular embedded in the material based on gelatin. The reinforcing materials should be physiologically compatible and at best likewise resorbable.

Depending on the kind of reinforcing material, stability in respect of resorption mechanisms may be controlled to a certain extent along with control of the mechanical properties. In particular, resorption stability of the reinforcing materials may be selected independently of the other constituents of the nerve guide, for example the material based on gelatin.

The reinforcing materials show a marked improvement in the mechanical properties of the nerve guides, even at fractions of 5% by weight (relative to the dry mass).

Above fractions of 60% by weight, there is as a rule no further significant improvement to be achieved and/or the desired resorption properties or also the necessary flexibility of the nerve guides may be achieved only with difficulty.

The reinforcing materials may be selected from particulate and/or molecular reinforcing materials, as well as mixtures of these.

For the particulate reinforcing materials, the use of reinforcing fibers is especially recommended. For this, there are recommended in particular polysaccharide fibers and protein fibers, such as for example collagen fibers, silk and cotton fibers, as well as polyactide fibers or also mixtures of any of the foregoing.

On the other hand, molecular reinforcing materials are also suitable, in order to improve the mechanical properties, and, if desired, also the resorption stability of the nerve guide.

Preferred molecular reinforcing materials are in particular polyactide polymers and their derivatives, cellulose derivatives, and chitosan and its derivatives. Also molecular reinforcing materials may be used as mixtures.

Preferably the shaped body of the nerve guide comprises at least a part of the reinforcing material or materials. For this, the reinforcing materials are embedded in a matrix of the material based on gelatin, or are present in a molecular mixture comprising the material based on gelatin.

Preferred embodiments of the nerve guides have a multi-layered shaped body, it being possible for the individual layers to be provided with specific functions, as will be explained in more detail further below. For example, one of the layers may function as the semipermeable layer.

Surprisingly, it has also become apparent that material based on gelatin, in particular gelatin of high molecular weight, has a angiogenesis-promoting effect, so that the formation of capillary blood vessels is also promoted at the same time along with the actual basic function of providing a nerve guide for the growth of nerves by the implantation of the nerve guide according to the invention, so that the environment of the nerve guide, i.e. the newly developing axons, are increasingly supplied with nutrients.

In the nerve guide according to the invention, the material based on gelatin preferably comprises gelatin as main constituent, this meaning that gelatin represents the greatest fraction of the material compared with possible other additional constituents such as for example other resorbable polymers, such as for example polysaccharides or hyaluronic acid. For this calculation, as also in the case of the more specifically recommendations given in the following text, fractions of reinforcing material which may be present are not taken into account.

More preferably, gelatin represents the preponderant fraction of material based on gelatin.

Still more preferably, gelatin represents substantially the entirety of the material based on gelatin.

The gelatin of high molecular weight preferably used in the material based on gelatin preferably has a Bloom value of about 160 g to 300 g.

Tests with gelatin fractions of low molecular weight show that their angiogenesis-promoting effect is markedly less than that of gelatin of high molecular weight.

Gelatin of high molecular weight also provides further advantages in the material based on gelatin, these being discussed in more detail in the following text in respect of the question of setting the level of cross-linking.

More preferably, a gelatin is used which is low in endotoxins, pig skin gelatin being in particular suitable for this. A gelatin of this kind preferably has an endotoxin content, as determined by the LAL test (see the fourth edition of the European Pharmacopoeia, Ph. Eur. 4) of 1,200 I.U./g or less, in particular even 200 I.U./g or less. By especially careful work, endotoxin contents of for example 140 I.U./g or even down to 50 I.U./g may even be achieved.

Gelatin of different origin or prepared by other methods may have endotoxin values of up to more than 20,000 I.U./g.

According to the invention, careful selection from among approved raw materials, in particular only freshly isolated and delivered pig skin and exclusion of the use of refrigerated products, immediate use of raw material without longer periods of transport or storage, separate cleaning of the entire production installation before beginning production of the special batches, optionally including use of ion exchangers and filter systems, contributes to a drastic lowering of the endotoxin value.

The nerve guides according to the invention typically have lengths in the range from 0.5 to 50 cm. In the case where the nerve guide has a single hollow tubule as shaped body, this has an outer diameter of about 1 to 30 mm. The wall thickness, depending on whether the shaped body is single-layered or multi-layered, is for example 0.02 to 5 mm.

If the nerve guide had a plurality of hollow tubules/shaped bodies, the outer diameter is in each case preferably in the range from 100 to 800 μm. In a normal nerve, small groups of axons are present in so-called fascicles. A nerve guide with a plurality of shaped bodies having the above-mentioned preferred diameters emulates this structure.

Production of hollow bodies in the form of tubules from material based on gelatin presents a special challenge. In particular, production of nerve guides for regeneration of nerves in the peripheral nervous system demands relatively small dimensions. At the same time, the dimensions must be obtainable in a reproducible manner and the production method should not be over-expensive A preferred method comprises a dipping procedure in which a mandrel is dipped one or more times into a solution of material based on gelatin and in between, is left to dry, at least partially.

Removal of the hollow tubules thus produced for use as shaped bodies for nerve guides according to the invention is difficult however because of the small diameters and wall thicknesses.

It is preferred therefore to produce a hollow body with a greater diameter and wall thickness in a first step and then to stretch this hollow body in its longitudinal direction into a hollow tubule with the desired outer diameter and the intended wall thickness.

Stretching materials based on gelatin has up to now not been described in the literature to any significant extent. It is also apparent that a material based on gelatin, in particular gelatin itself, cannot be stretched successfully, without modification.

According to the invention, the material based on gelatin is therefore preferably used with a fraction of plasticizer which is in the range between 12 to 40% by weight, in particular in the range from 16 to 25% by weight.

At the same time, use of plasticizer leads, as expected, to greater flexibility of the nerve guide, by virtue of which handling is simplified during insertion as an implant.

Most surprisingly, gelatin which contains fractions of this level of plasticizers, can be stretched with a relatively large stretch ratio, this being in practice from 1.4 to 8.

Preferred plasticizers according to the invention for the material based on gelatin are in particular selected from glycerin, oligoglycerins, oligoglycols and sorbite. Plasticizers of this kind may remain in the material based on gelatin and are resorbed in the body of the patient in exactly the same way as the gelatin-based material of the nerve guide or the shaped body itself.

Very surprisingly, by use of plasticizers for stretching the materials based on gelatin, an increase in their tear strength in the longitudinal direction of the nerve guide is also achieved, rising in particular to a value of 30% or more, in particular even 50% or more.

In use of the nerve guide according to the invention as an implant for regeneration of nerves, this provides special advantages for the surgeon, because he has at his disposal a relatively insensitive implant. Likewise, by stretching the cross-linked material, a tear strength in the longitudinal direction of 40 N/mm$^2$ or more, in particular 60 N/mm$^2$ or more, may be achieved.

Preferably, the material based on gelatin is used in a state in which it is at least partially cross-linked. The resorption stability of the nerve guide or shaped body may be adjusted by the degree of cross-linking.

Cross-linking preferably pertains to the gelatin comprised in the material based on gelatin.

For the recommended dipping method for producing hollow bodies, the material based on gelatin is already pre-cross-linked in the solution. This leads to a uniform degree of cross-linking in the entirety of the material based on gelatin.

It is further preferred for the finished shaped body, which as a rule been stretched, to be further cross-linked in a second step, in order to thereby ensure the desired resorption stability. This two-stage cross-linking allows higher levels of cross-linking than single-stage cross-linking. In this there is then also the possibility of effecting gradated degrees of cross-linking.

For example, the degree of cross-linking of the material based on gelatin may be higher in the wall of the shaped body neighboring the external surface than in the regions of the wall neighboring the lumen.

Based on the choice of a different degree of cross-linking at the external surface of the shaped body on the one hand and, on the other hand, neighboring the lumen of the shaped body, it is possible, in regeneration of nerve fibers, i.e. during the development of axons, for there to be provided in first instance, on the one hand a protected volume in the form of the lumen, which can increase in size in the course of growth of the nerve because of the progressive resorption of the material based on gelatin. Nonetheless, the protective function of the nerve guide is still maintained, because the outwardly located regions of the wall of the shaped body are resorbed more slowly and can therefore provide protection for a longer period against inward migration of fibroblasts.

This allows regenerating axons to form myelin layers which become increasingly thicker and provide isolation without pressure building up in the nerve guide, which can damage regenerating axons.

The at least partial cross-linking in the solution may be carried out both chemically and also enzymatically, as can the second cross-linking step.

For chemical cross-linking, there may be used as cross-liking agent in particular aldehydes, dialdehydes, isocyanates, diisocyanates, carbodiimides and alkyl halides.

Particularly preferred is cross-linking using formaldehyde, since there is achieved in the respective cross-linking step simultaneous sterilization of the material based on gelatin and the shaped body.

For enzymatic cross-linking, transglutaminase is preferably used.

For the purpose of using the nerve guide, the degree of cross-linking is selected so that the nerve guide, in particular its shaped body, exhibits a reduction in dry weight of at most about 20% by weight over a period of 4 weeks, under standard physiological conditions (PBS buffer pH 7.2; 37° C.).

The lumen of the shaped body is extremely large compared with the dimensions of naturally occurring individual nerve fibers. Axons are only about 1 μm thick, while the lumen provided by the nerve guide can have a diameter of up to 10 mm. Even when several tubules are used in a nerve guide, their respective lumens provide a clear width which exceeds the thickness of the axons by an order of magnitude of about 2 or more.

In order to further promote target-oriented growth of axons during regeneration and to keep the time for regeneration as short as possible, one or more guide elements are preferably disposed in the lumen of the shaped body, aligned parallel to its longitudinal direction. The guide element or elements then preferably extend(s) substantially over the entire length of the lumen.

The guide elements may then be already populated with auxiliary cells, in particular Schwann cells, these promoting growth of axons.

Schwann cells are found in natural nerves; they release growth factors by way of controlled feedback loops and promote both formation of blood vessels and regeneration of axons. These cells may for example be isolated from the injured nerve of a patient and reimplanted by way of the nerve guide according to the invention, following cultivation in vitro. In order for the Schwann cells to be arranged in the most uniform distribution possible in the lumen of the nerve guide, the Schwann cells are preferably placed in a matrix of a gelatin gel, which is liquefied at a raised temperature (for example 40° C.) and gelled again during cooling to body temperature, and the cells admixed at higher temperature are immobilised. In this way, the Schwann cells can be applied to the guide element in a uniformly distributed manner and remain held in this condition after cooling to room temperature until the implant is used in the patient.

In order not to hinder growth of axons and differentiation of nerve tissue, the guide elements should occupy preferably at most about 30% by volume of the lumen.

Microfilaments with average thicknesses from about 10 to 100 µm are especially suitable as guide elements, depending on the clear width available in the lumen.

In order to be able to arrange a plurality of microelements in a uniformly distributed manner in the lumen, the elements are preferably stabilized in a matrix or at a spacing with respect to one another by means of spacers.

An especially effective guide function is observed in the case of guide elements which have guide grooves. As a result of this, there arises a stereotropic effect and the optionally used auxiliary cells as in the so-called Büngner bands can be settled with very good longitudinal alignment. After this, there is obtained likewise high-grade, longitudinally oriented growth of axons. The geometric dimensions are not especially critical and may, for example, have a depth of 0.5 to 50 µm. More important is the presence of edges which delimit the guide grooves.

If a matrix is used to fix the microfilaments with respect to one another, the material of the matrix should preferably be formed from a material which inhibits growth of axons, to that their growth is oriented exclusively on the microfilaments. Materials which inhibit growth of axons are for example hyaluronic acid or also hydrophobic gelatin gels.

Alternatively, a guide element may be made from a rolled-up planar material, which provides micro-channels between the layers of the roll, in a manner similar to the guide grooves of the microfilaments described above. The structure needed may be given to the planar material by casting it in a mold or by subsequent stamping or the like. The axis of rolling for the planar material is parallel to the longitudinal direction of the nerve guide.

By suitable configuration of the planar material, this may at the same time form the shaped body of the nerve guide.

As already discussed further above, the nerve guide may contain a plurality of shaped bodies, which are preferably bonded to each other by means of a matrix material. This matrix material preferably contains angiogenesis-promoting constituents, in order to facilitate the development of blood vessels between the axons, similar to the way in which this also occurs in the natural fascicles in a non-neuron matrix. This matrix material is preferably a material based on gelatin and preferably has an open-pored structure.

This matrix material takes up for example a volume fraction of 30 to 60% of the volume of the nerve guide. The matrix material is further preferably resorbable.

In a further preferred embodiment of the invention, the nerve guide has an outer sleeve or matrix mantle which surrounds the formed body or bodies and is likewise formed from a resorbable material. A porous, in particular open-pored, structure is especially recommended for the matrix mantle. The average pore size is preferably in the range from 100 to 300 µm.

The matrix mantle may be produced for example by foaming around the shaped body or bodies.

Alternatively the matrix mantle may be stamped out from a pre-prepared solid block of material, in particular a sponge, or obtained by means of a core drill. The through opening for introducing the shaped body, which has optionally previously been provided with the semipermeable layer, may easily be formed by a boring tool (when working with the core drill, this preferably takes place at the same time as the matrix mantle is produced).

The shaped bodies may be pushed into the matrix mantle formed in this way. A gentle press-fit between matrix mantle and shaped body suffices as a rule to enable safe handling of the nerve guide.

Preferably, the matrix mantle comprises an angiogenesis-promoting constituent in order to also promote formation of blood vessels around the nerve guide and in particular up to and onto the shaped body for the nerve guide. This stimulating action is preferably realised in such a manner that the sprouting of blood vessel takes place before the formation of axons in the lumen of the shaped body, or at least during their formation. Suitable materials for this are again materials based on gelatin, in particular based on gelatin of high molecular weight, as have been already described extensively further above. The thickness of the outer sleeve or matrix mantle is preferably 1 to 2 mm.

When a plurality of shaped bodies are used in the nerve guide, the matrix mantle may merge into the matrix bonding the shaped bodies to one another. Both matrices may be formed from the same material, in particular one which promotes angiogenesis.

In this case, the semipermeable layer is then part of each shaped body in order to ensure that no inward migration of cells which inhibit axon growth or even entirely prevent it, can take place into the lumen, this being reserved for axon growth.

The matrix mantle can for this have a higher rate of resorption than that of the shaped body or bodies.

The longer the distances to be bridged between two nerve stumps by an implant, the longer should be the resorption time for the materials of the shaped body based on gelatin. That is, the resorption property of the implant, in particular of the shaped body and especially of the semipermeable layer, should be determined based on the length of the nerve defect.

For nerve guides which are used as implants for the peripheral nervous system, the resorption property of the nerve guide may be selected such that the resorption of the implant begins at one end and progresses toward the other end, in accordance with and preferably determined by axon growth. Myelinisation and thereby thickening of the nerve fibers also begins from the end of the implant at which axon development begins. The space necessary for squashing of the nerve fibers to be avoided is created by virtue of the time-determined resorption of the implant.

Desired properties of this kind may also be achieved by way of varying the degree of cross-linking of the material based on gelatin along the longitudinal direction of the nerve guide, i.e. the degree of cross-linking is less at one end of the nerve guide than that at the other end, a step-wise variation of the degree of cross-linking or a substantially continuous increase in the degree of cross-linking being possible.

If by contrast the implant is used in the central nervous system, account is preferably taken of the circumstance that axon growth takes place outwardly from both of the nerve stumps. Here a gradated resorption behavior commends itself, in which resorption begins approximately simultaneously at both ends of the implant and the central region between the ends of the implant is only resorbed after a time delay.

Also this can be effected along the longitudinal direction of the nerve guide by corresponding gradation of the degree of cross-linking. Here also, stepwise variation of the degree of cross-linking may be selected or a substantially continuous gradation.

For practical considerations, it may be advantageous for the clear width of the lumen at the two ends of the nerve guide to be greater than for the rest of the region, by virtue of which the nerve stumps of the lesion can be introduced more easily into the nerve guide.

BRIEF DESCRIPTION OF THE SEVERAL VIEWS OF THE DRAWINGS

The invention will be explained in more detail on the basis of the drawing and the following examples. In the drawing:

FIG. 5 shows a schematic representation of a test set-up for testing the diffusion properties of a layer which is semipermeable according to the invention;

FIGS. 6 and 7 show diagrams of the experimental results for the test of the diffusion properties of the layer which is semipermeable according to the invention;

FIG. 9 is a diagram for showing the development of blood vessels in material for promoting angiogenesis.

FIG. 1 shows a nerve guide designated as a whole by the reference numeral 10 which has a shaped body 12 made from a material based on cross-linked gelatin. The shaped body 12 has a tubular hollow body with a wall 14, this having an external surface 16 and an internal surface 18 defining a hollow space 20 called a lumen.

Figure 1:
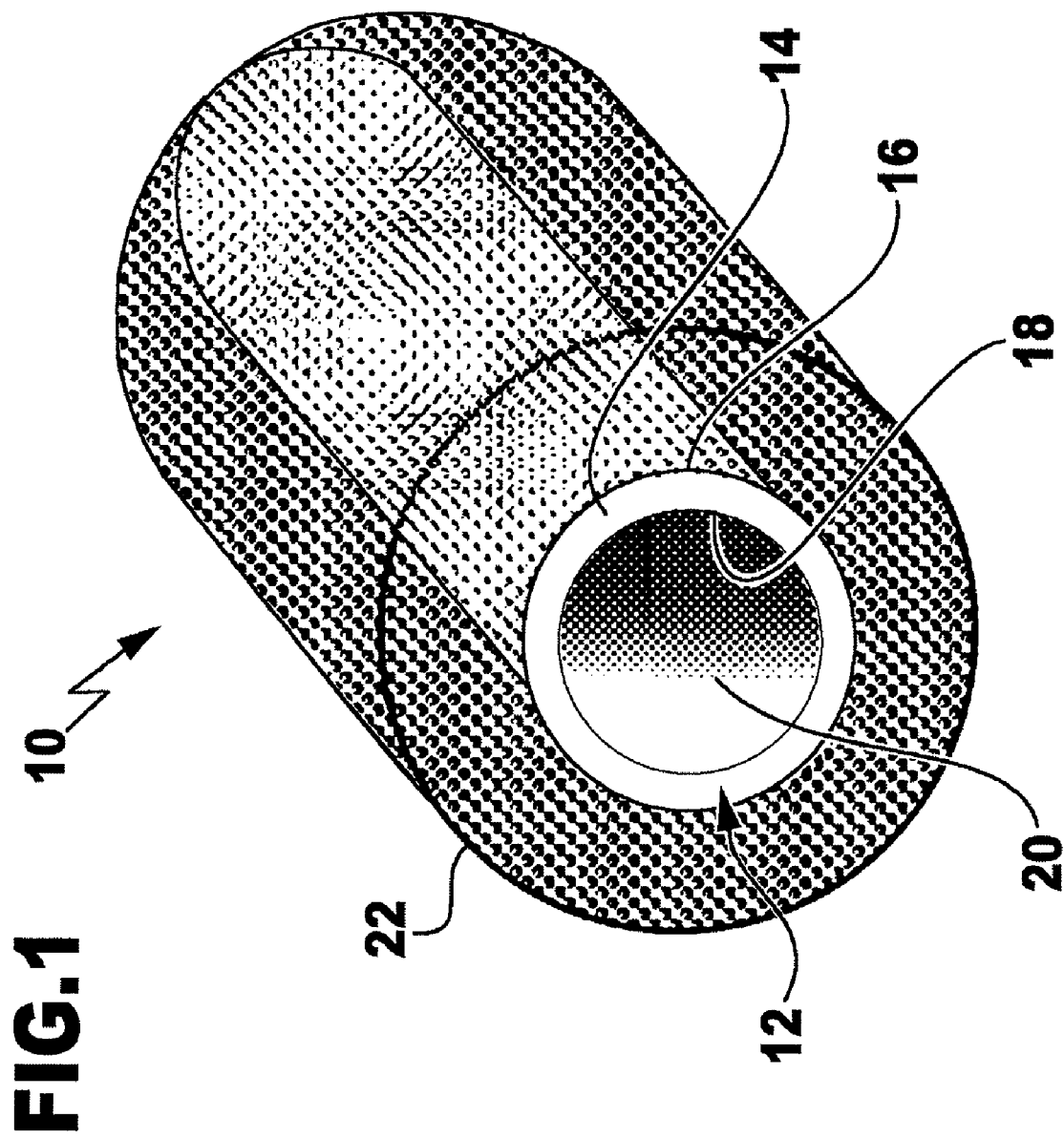
FIG. 1: shows a schematic representation of a nerve guide according to the invention in a first embodiment.

The nerve guide further has a semipermeable layer, which is formed integrally with the shaped body 12 (this not being shown in detail in FIG. 1). The position of the semipermeable layer is immediately inside the wall 14, preferably adjacent to the external surface 16.

The external surface of the shaped body 12 is surrounded by an outer sleeve 22, which is formed to be open-pored and comprises a constituent which promotes angiogenesis, in particular a cross-linked gelatin of high molecular weight which has a sponge structure.

The outer sleeve 22 may be produced from a sponge material made from cross-linked gelatin, this being described in detail in the following Example 3. Initially, a block of sponge material of this kind of sufficient thickness is prepared (to correspond to the length of the finished nerve guide). The outer sleeve 22 is produced from this block as a hollow cylinder, for example by stamping or by means of a core drill. The shaped body 12 can then be pushed into the opening extending through this hollow cylinder, the shaped body preferably being held in the outer sleeve 22 with a light press-fit.

Figure 2:
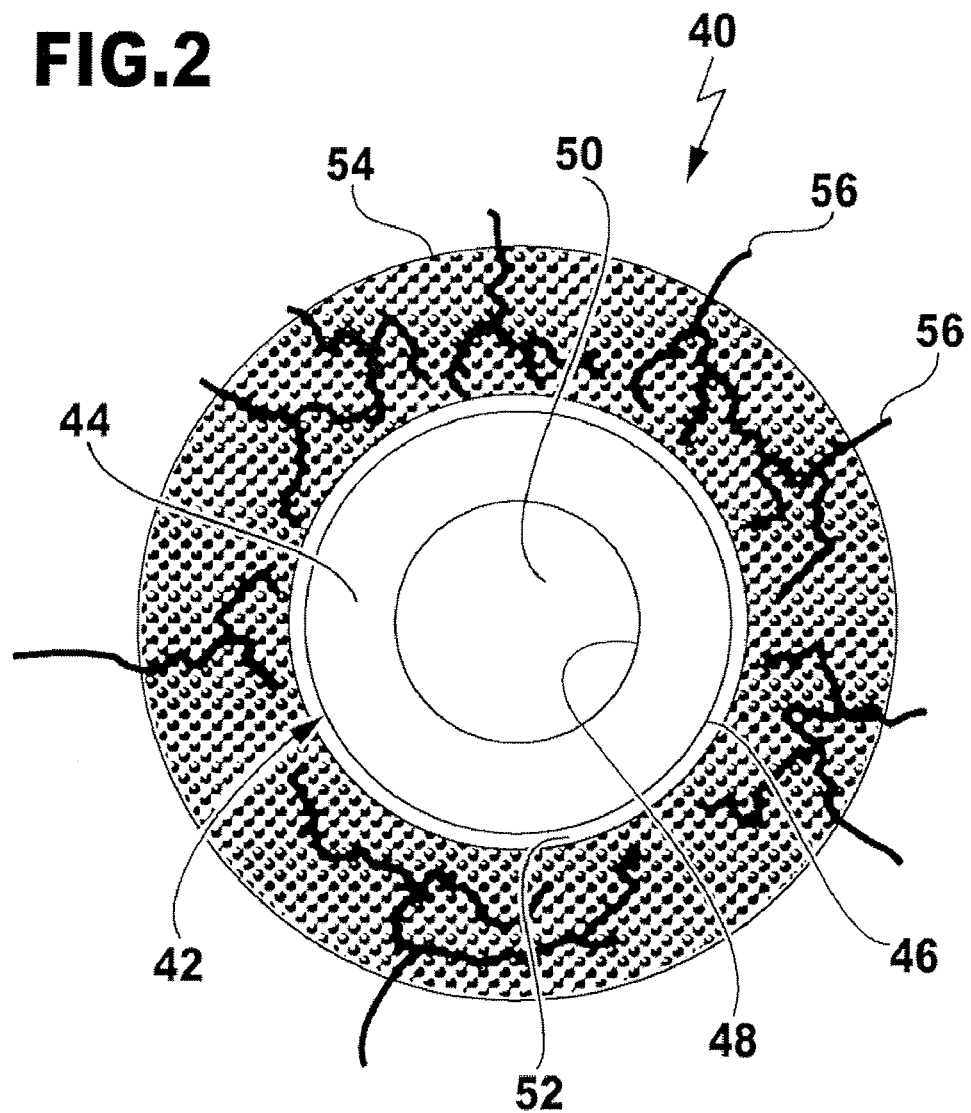
FIG. 2: shows a schematic representation of a nerve guide according to the invention in a second embodiment.

FIG. 2 shows a further nerve guide 40 according to the invention with a tubular hollow body as the shaped body 42. The shaped body 42 has a wall 44 made from a material based on gelatin, the wall having an external surface 46 and an internal surface 48 which defines a lumen 50.

A separate semipermeable layer 52 is located neighboring the external surface 46 of the shaped body 42, this allowing nutrients and gases to diffuse through it, but blocking penetration of cells, in particular fibroblasts.

The shaped body 42 with the semipermeable layer 52 is then surrounded outwardly by an outer sleeve 54, which is formed similarly as is described in respect of the embodiment of FIG. 1. The outer sleeve 54 may be made and slid onto the shaped body 42 as described in connection with the embodiment of FIG. 1.

FIG. 2 shows schematically the inward sprouting of blood vessels 56 into the outer sleeve, which is already taking place and is encouraged by the angiogenesis-promoting constituents of the outer sleeve 54.

EXAMPLES

Example 1

Production of a Nerve Guide According to the Invention

Production of a Tubular Hollow Body

In the following text, there is first of all described the production of a hollow body in the form of a tubule, which is the basic feature of a nerve guide according to the invention. The different types produced have internal diameters of about 2,000 μm, 1,100 μm and 150 μm and are produced by means of the dipping method favoured according to the invention and are subsequently stretched.

For this, 100 g of pig skin gelatin (Bloom strength 300 g) was initially dissolved at 60° C. in a mixture of 260 g of water and 40 g of glycerin as plasticizer and the solution was degassed by means of ultrasound. This corresponds to a fraction of plasticizer in the material of about 29% by weight, based on the weight of gelatin and glycerin.

After addition of 4 g of an aqueous, 2.0% by weight formaldehyde solution (800 ppm of cross-linker based on the gelatin), the solution was homogenized, again degassed, and the surface freed of foam. A stainless steel mandrel, serving as a shaped element and having a diameter of 2 mm, which had previously been sprayed with a separating wax, was dipped briefly into the solution thus produced to a length of about 3 cm. After the mandrel was withdrawn from the solution, it was rotated, so that the solution adhering formed as uniform a layer as possible.

After drying for approximately one day at 25° C. and a relative humidity of 30%, the formed hollow tubule was removed from the mandrel.

The hollow tubule produced in this way had an internal diameter of 2 mm, corresponding to the diameter of the mandrel, and an average wall thickness of 300 μm, as was established by optical microscope.

In order to bring the hollow tubule to a still smaller internal diameter, it was stored for five days at 23° C. and a relative humidity of 45% and then stretched.

For stretching, the tubule was gripped at both ends and softened by the action of hot steam. In this thermoplastic condition, it was lengthened with a stretch ratio of about 1.4, fixed in this condition, and dried over a period of 16 hours at 23° C. and a relative humidity of 45%.

The hollow tubule thus obtained had an internal diameter of about 1,100 μm and a wall thickness of about 200 μm. Examination by optical microscope showed the cross-sectional shape formed to be extremely regular and also that the wall thickness of the tubule was very uniform, seen over its periphery and its length.

With greater stretch ratios, hollow tubules with internal diameters down to 150 μm were obtained.

In order to prolong the time for physiological degradation of the tubule, the gelatin contained in it was submitted to a further cross-linking step. For this, the tubule was exposed, in a dessicator, for 17 hours, to the equilibrium vapor pressure of an aqueous formaldehyde solution of 17% by weight, at room temperature.

For this, the ends of the tubules may be closed, so that the cross-linking is effected only from the external surface inward. There is then found here a higher degree of cross-linking at the external surface compared with the internal surface which defines the lumen of the tubule, and a correspondingly higher resorption stability.

A hollow tubule with a higher degree of cross-linking in the wall region neighboring the lumen may for example be obtained by the formaldehyde vapor being conducted exclusively through the lumen of the hollow tubule.

Alternatively or in addition, different degrees of cross-linking may also be realised by the mandrel being dipped successively into solutions with different concentrations of cross-linking agent. In this way, there results a correspondingly gradated degree of cross-linking over the wall thickness of the hollow tubule.

It will be understood that the properties of the hollow tubules described here may be modified in many different ways, in that in particular the size and shape of the mandrel, the fractions of gelatin, plasticizer and cross-linking agent in the solution, the number of immersion steps, and the intensity of the subsequent cross-linking may be adapted to the particular requirements.

Production of the Semipermeable Layer

The external surface of the hollow tubule described above may for example be modified chemically in order to create a semipermeable layer which surrounds the lumen and is integral with the hollow tubule.

Thus for example the amino groups of lysine residues may be converted into a succinated form by means of succinic anhydride, the $pK_s$ value of the gelatin material falling from 8 to 9, which are the values found for the unmodified material, to about 4.

A further possibility for modifying the gelatin consists in converting the amino groups of lysine residues into dodecenyl succinyl groups. The $pK_s$ value in this case falls to about 5 and at the same time a slight hyrophobisation of the gelatin takes place.

In both cases, the cell adhesion of fibroblasts to a surface treated in this way is markedly reduced, as will be explained in more detail in the experiments described in the following text and in connection with FIGS. 3 and 4.

First of all it should be noted for the sake of completeness that in the case of the hollow tubule produced as described above, the tubule may be provided with a separate semipermeable layer, as an alternative to modification of the gelatin of the external surface. In order to remain within the terms of the examples selected above, this layer may be effected by application of a succinated or dodencyl-succinated gelatin or mixtures of these with other biopolymers, in particular also unmodified gelatin in an aqueous solution. The procedure may here follow the immersion method, as was further described above for the production of the hollow tubule.

The degree of conversion of the lysine groups for the modified gelatin amounts preferably to 30% or more.

In the case of dodencyl-succinated gelatin, degrees of conversion of 40 to 50% are often sufficient, whereas in the case of succinated gelatin, more like 80% to almost complete conversion of the lysine groups delivers the best results.

Figure 3:
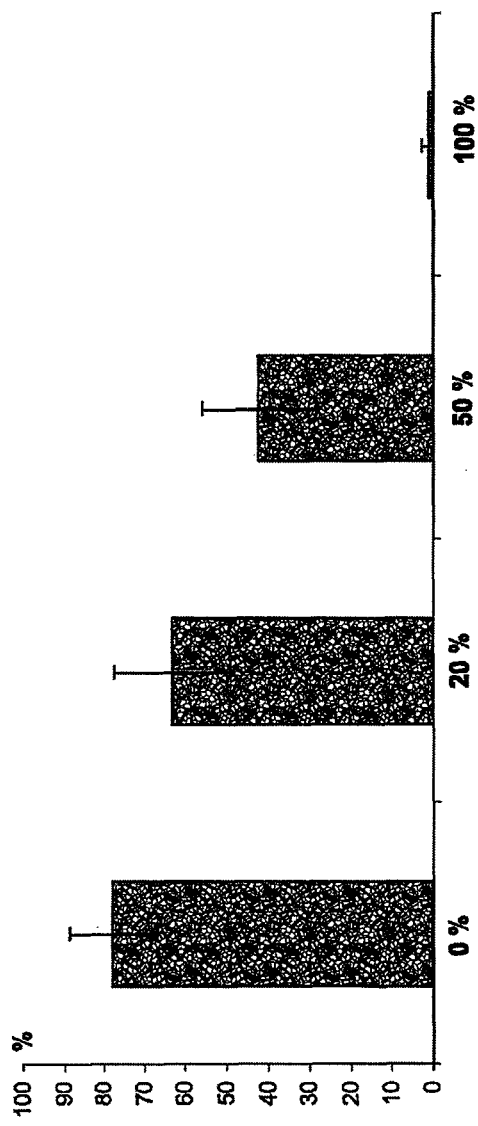
FIGS. 3 and 4 show diagrams relating to the effect of gelatin modified according to the invention on the cell population of a substrate.
Figure 4:
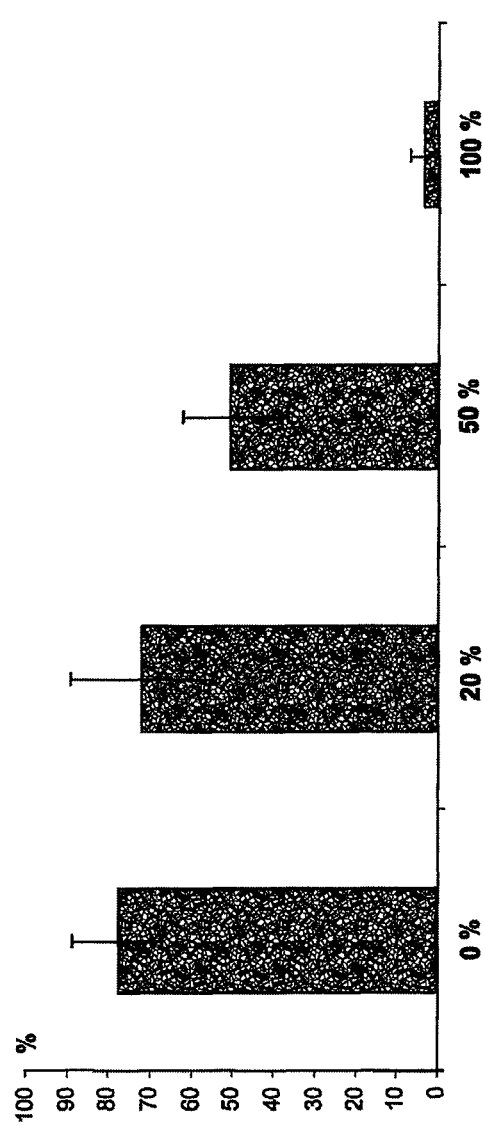

FIGS. 3 and 4 show cell adhesion results for test surfaces of gelatin materials, applied for test purposes to glass surfaces, the gelatin materials having been produced starting from pig skin gelatin (MW 119 kDa) and a gelatin (FIG. 3) succinated at the lysine groups up to about 95%, or about 45% of dodecenyl-succinated gelatin (FIG. 4) of the same type. In each case, mixtures of unmodified gelatin with modified gelatin in ratios of 100:0, 80:20, 50:50 and 0:100 were tested.

In the tests, in each case 20,000 porcine chondrocytes were incubated on a test surface for a period of 4 h at 37° C. The excess was removed, the surface washed and the cells remaining on the surface fixed in order for them to be subsequently evaluated by optical microscope. Comparable results were obtained with human chondrocytes.

The percentage values in the diagrams represent the fraction of cells found on the film test surfaces compared with the number used for the incubation, after the above-mentioned procedure had been carried out.

For both types of modified gelatin, population effects were close to zero in the case of modified gelatin being used exclusively.

From this it may be concluded that in the case of the surfaces of the hollow tubule being modified, comparable effects are achievable for a correspondingly high degree of conversion of the lysine groups accessible on the external surface.

A corresponding result is naturally the case for application of a separate layer of modified gelatin to the external surface of the hollow tubule.

Since migration of cells into the wall of the hollow tubule initially requires them to adhere to the external surface, conditions for blocking action for cells are very well fulfilled, as is to be expected, according to the invention, by a semipermeable layer.

Example 2

Semipermeable Property/Blocking Layer Function of the Gelatin Film Based on Planar Material Tests In order to test the diffusion properties of the test films described above, the films were tensioned between two blocks 62 and 64 in a two-chamber test apparatus 60, as is to be seen from FIG. 5, cavities 68, 70 being provided in the blocks 62 and 64 on both sides of the test film 66, the cavities being flushed with different media during the test phase.

The upper chamber 68 was filled with a phenol red solution as a substitute for a nutrient solution, a pure PBS solution being used in the lower chamber 70. Every two hours, the absorption of phenol red and the PBS solution were measured. The measured values are shown in the curves of FIG. 6 for a film of unmodified gelatin.

The trial was repeated with a film which was first of all populated with 10,000 cells/cm$^2$, these being given 2 hours for adhering. The adhered cells were multiplied on the film for a week in culture, after which the same measurement as described above was carried out. The measured values are shown in FIG. 7.

In the result, there is found a reduction of the phenol red concentration in the upper chamber 68 and a corresponding increase in the phenol red concentration in the lower chamber 70, corresponding to diffusion of nutrient through the film. In the case of the cell-populated film, there resulted a tendency toward accelerated diffusion of the phenol red.

Parallel to this, there was found no passage whatever through the films for suspensions of carbon particles (particle size for 75% by weight, less than 45 μm). This means that even when the cells are populated, the film still provides an active blocking layer against penetration by cells and particles and is not put out of action by cellular proteases.

The present results could also be confirmed in culture trials lasting two and three weeks.

Example 3

Angiogenesis Effect

Production and Properties of Shaped Bodies Having a Cell Structure Based on Cross-Linked Gelatin Five formulations of a 12% by weight solution of pig skin gelatin (Bloom strength 300 g, average molecular weight 140 kDa) in water were prepared by dissolving gelatin at 60° C., degassed by means of ultrasound, and in each case the appropriate quantity of an aqueous formaldehyde solution was added (1.0% by weight, room temperature), so that 1,500 ppm of formaldehyde were present (relative to the gelatin). In the case of a sixth formulation, no addition of formaldehyde took place.

The homogenized mixtures were heated to 45° C. and after a reaction time of 10 min, were foamed mechanically with air. The foaming step, which was of about 30 minutes duration, was carried out for the six formulations with a different ratio of air to gelatin solution, cell structures with different wet densities and pore sizes being obtained in accordance with Table 1.

The foamed gelatin solutions, which had a temperature of 26.5° C., were cast in molds with dimensions to 40×20×6 cm and dried for about four days at 26° C. and a relative humidity of 10%.

The dried shaped bodies for all six formulations have a spongelike cell structure (called a sponge in the following text). They were cut into 2 mm thick layers and exposed, for the second cross-linking step, for 17 hours in a dessicator, to the equilibrium vapor pressure of an aqueous formaldehyde solution of 17% by weight, at room temperature. For the sixth formulation, this represented the first (and only) cross-linking step. In order to achieve uniform purging of the entire volume of the shaped body, the dessicator was for this in each case evacuated two to three times and recharged with air.

The pore structure of the sponges was ascertained by optical microscope and could be confirmed by a scanning electron microscope.

TABLE 1

| Formulation | Wet density (mg/cm$^3$) | Dry density (mg/cm$^3$) | Average pore size (μm) |
|---|---|---|---|
| 1-1 | 100 | 20 | 250 |
| 1-2 | 175 | 27 | 200 |
| 1-3 | 300 | 50 | 125 |
| 1-4 | 530 | 70 | 100 |
| 1-5 | 600 | 100 | 75 |
| 1-6 | 78 | 12 | 300 |

In order to determine the stability of the sponges, pieces of 30×30×2 mm were weighed out, each put in 75 ml PBS buffer and stored at 37° C. After the respective storage time, the pieces were washed in water, dried and weighed.

While the sponge 1-6 had already fully dissolved after three days, all of the sponges which had undergone two-stage cross-linking were still extant up to more than 80% even after 14 days. Considerable differences in the further breakdown behavior appears however, which is ascribed to the different foam densities of the materials. Thus sponge 1-1 is fully dissolved after 21 days and sponge 1-2 after 28, while sponges 1-4 and 1-5 are still largely extant even after 35 days. There thus results the further possibility of controlling in a targeted manner the breakdown behavior of these sponges or cell structure materials independently of other parameters.

The properties of the cell structure materials may however also be markedly modified by change of the concentration of gelatin on the starting solution.

Higher concentrations of gelatin lead to wider (thicker) cell walls or partitions between the individual pores, which shows up in increased ultimate strength of the corresponding sponges.

The stability of the shaped body, in particular in respect of proteolytic breakdown, may by contrast be controlled by way of the degree of cross-linking, i.e. by the choice of concentration of cross-linking solution.

Evidence for the Angiogenesis-Promoting Effect

Samples having dimensions of 15×15×2 mm were produced from shaped bodies obtained by a procedure analogous to the foregoing and cross-linked twice (dry density 22 mg/ml, average pore diameter about 250 μm), referred to below as implants.

Figure 8A:
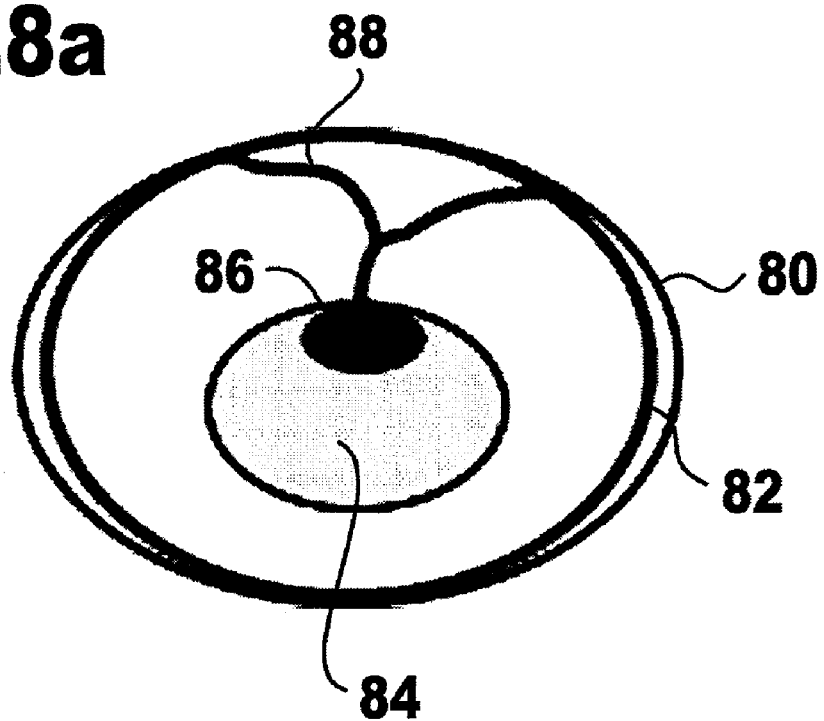
FIGS. 8a and 8b show a schematic representation of the experimental arrangement for investigating angiogenesis by means of a choriollantois membrane.
Figure 8B:
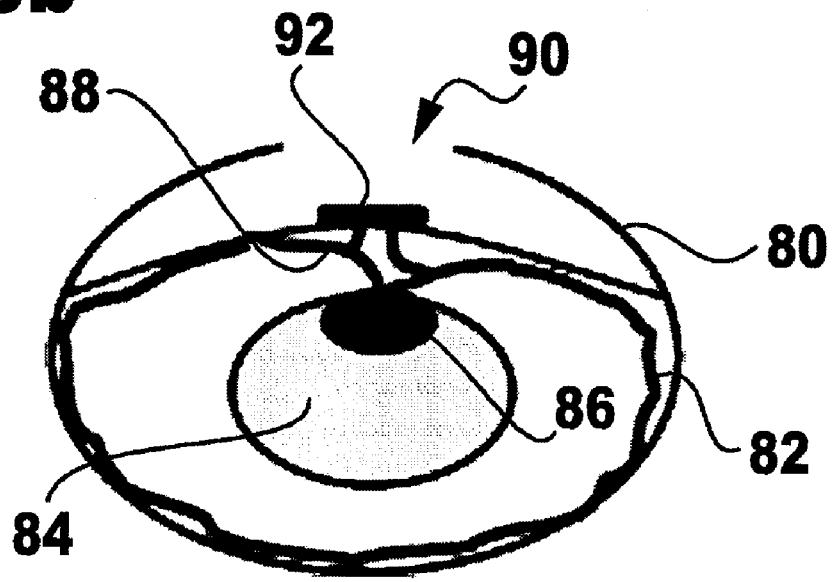

The angiogenesis-promoting properties of these implants were investigated by means of a test on fertilised hens' eggs, schematically illustrated in FIGS. 8a and 8b.

FIG. 8a shows schematically the structure of a hen egg in cross-section. Beneath the shell 80 is the choriallantois membrane 82 (referred to below in short as CAM). Starting from the embryo 86 located at the edge of the yolk 84, there takes place the formation of extraembryonal blood vessels 88, which spread out along the CAM. If part of the egg white is removed by means of a cannula, a window 90 can then be cut in the shell 80 without damaging the CAM 82 (as illustrated in FIG. 8b). Now an implant 92 can be placed onto the CAM 82 and the action of the implant on blood vessel formation investigated (see for example J. Borges et al (2004) Der Chirurg 75, 284-290).

Reorientation of blood vessels and emergence of new blood vessels are observed in images taken using an optical microscope after 3, 5 and 7 days.

As reference examples, along with the substrate according to the invention, comparable spongelike materials from collagen (renatured bovine collagen, density 5.6 mg/cm$^3$, obtainable from the Innocoll company) and poly-DL-lactide (producer ITV Denkendorf) were tested.

All implants were placed on a CAM and the number of blood vessels which had developed in the direct vicinity of the implant was determined after 3, 4, 5, 6 and 7 days. Within a few days, the blood vessels had aligned themselves very clearly onto the angiogenesis-promoting substrate or the reference samples of sponge-like collagen and poly-DL-lactide.

It appears that in the case of all three samples, a markedly higher number of blood vessels is present compared with the null value (CAM without an implant placed on it), similar effects having been achieved for all three samples, in particular seen in comparison with the null value.

This means that all of the materials tested were at about the same increased level in their angiogenesis-promoting action in their environment. The observed effect was brought about over quite some distance and probably therefore depends on so-called diffusible factors.

CAM is a tissue which represents the boundary surface between air and egg liquid. Possibly, activation of receptors results only from the mechanical stimulation of the substrate being laid on the CAM, which may lead to a release of pro-angiogenic factors such as for example VEGF to the cells. By this, endothel cells may be attracted and there would then result blood vessel formation directed onto the implant.

Another possible explanation is that entry of oxygen from the air to the epithet tissue is prevented by the placement of the implant. A so-called anoxia results in the region of the implant since less oxygen is available in the epithet tissue. On an anoxia, cells typically react by the release of VEGF, by which a conversion of blood vessels is induced or formation of new blood vessels. This means that the under-supplied part of the cells organise new supply channels. This biological phenomenon probably occurs above a critically under-supplied (deformed) tissue surface.

This would explain why in trials in which the mere placing of narrow rubber rings onto the CAM (very small overlaying surfaces), no pro-angiogenic effects could be observed.

In FIG. 9, the area of the blood vessels (in µm²) within the substrates or implants of the comparison materials and within the angiogenesis-promoting substrate of the present invention after 3, 5 and 7 days is set out. The sequence gelatin sample, collagen sample, poly-DL-lactide sample applies to the succession of columns illustrated.

As can be seen from FIG. 9, after 3 days only in the case of the angiogenesis-promoting substrate according to the invention is there a measurable fraction of blood vessels in the implant itself, while in the collagen sponge and the poly-DL-lactide sponge no measurable fraction of blood vessels is present.

The measurable blood vessels after 5 days show a very great increase for the angiogenesis-promoting substrates according to the invention, while for the poly-DL-lactide sample and the collagen sponge, no effect at all is observed.

After 7 days, the fraction of blood vessels in the implant for the angiogenesis-promoting substrate according to the invention falls away markedly, but the effect is about twice as great as after 3 days. At this time, it is observed that for the collagen sponge, there is still no measurable result, while for the poly-DL-lactide sponge an effect now appears, such as was already established for the gelatin sponge implant sample according to the invention after only 3 days.

In order to evaluate the samples and determine the number of blood vessels in the implants, frozen sections were prepared from each of the samples and colored with DAPI, in order to analyse the surface of the blood vessels within the sample. Images were then made from the central region of the sections and then quantitatively evaluated by image processing methods. For the collagen sponges, no blood vessel formation at all could be observed in the central region. For the poly-DL-lactide sponges, only after 7 days could angiogenesis be detected, coupled with progressive population by cells of connective tissue. Overall however, population with cells progressed significantly slower in the case of this comparative sample than for the implants according to the invention.

The regression of the blood vessels for the implant according to the invention after 7 days is revealed by a diminution in the measured surface. This may be due to the blood vessel network being again reduced to the extent that is actually needed for the implant region, because for example, relatively few other types of cell requiring to be supplied have migrated in. This equates to a process already found in the case of infections where a blood vessel network is rebuilt again as soon as inflammation subsides.

Example 4

Figure 10:
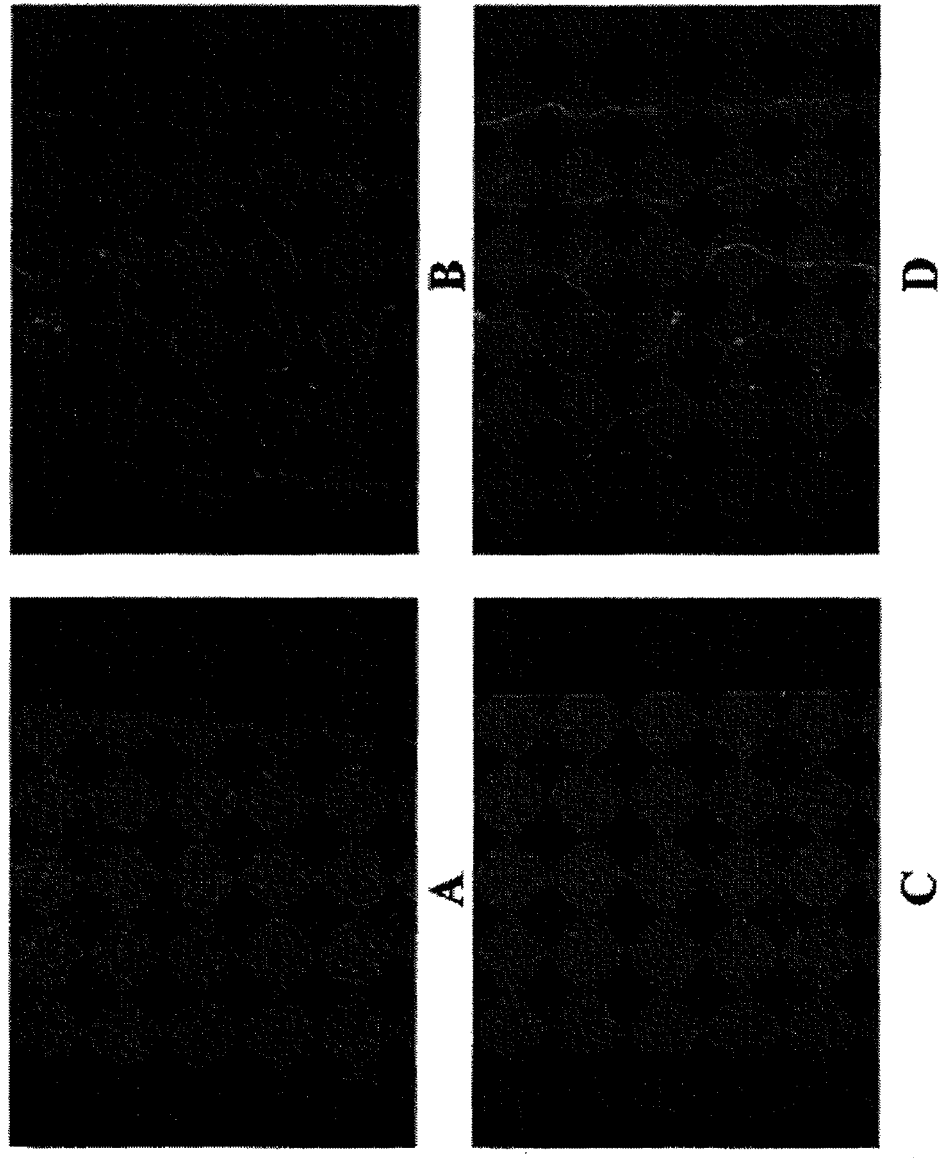
FIG. 10 is an image, taken using an optical microscope, of Schwann cells and axons cultivated on an inert plastics film.

Semipermeable Property of a Gelatin Tubule Allows Survival of Encapsulated Cells It was to be investigated whether cells survive in a closed tubular shaped body of gelatin (produced in accordance with Example 1, 1,100 µm internal diameter, wall thickness 200 µm, cross-linked twice). For this, a shaped body was stored for one week in PBS in order to wash it. Schwann cells were then seeded-out onto 0.9 mm wide, transparent inert plastics strips (uncoated X-70 copying film with a thickness of 0.1 mm from the folex imaging company). The plastics strips were pre-cleaned with PlasmaCleaner and coated with poly-lysine and laminin (33 µg/ml, 1 h at 37° C.). Schwann cells isolated from the ischias nerve of the rat (25,000 cells/cm²) were then seeded-out onto the film and held in a culture for 24 h. After this, individual neurones from dorsal root ganglions of the peripheral nervous system were prepared and seeded-out, with the Schwann cells, onto the plastics strips at a density of 10,000 cell/cm². The neurones were allowed to adhere for 4 h, after which the plastics strips with the cells on them were introduced into the shaped body of gelatin. Introducing the cells into the shaped body on the transparent plastics strips rather than directly has the great advantage that the plastics strips may be withdrawn without difficulty later on, in order to determine cell vitality using a microscope. The tubular shaped body was then closed at the ends by stoppers of dental wax (Rosa Dura, Kem-Dent, GB) and put in culture for 5 days. Under these conditions, nutrients and oxygen can only reach the cells through the wall of the shaped body. After 5 days exposure to culture, the plastics strips were removed from the tubes and marked with the antibody SM131 (Sternberger Monoclonals, USA) for detection of axons and DAPI as evidence of cell nucleii. As control, there served cell-populated plastics strips which were treated in exactly the same way but were not encapsulated; rather they were cultivated in an open condition in the same medium (DMEM, 10% FCS, glutamin, gentamycin). As is to be seen on the images of FIG. 10, taken using an optical microscope, the cells/neurones survive equally well inside and outside the shaped body (images A and C). This is to seen at the bright points. Axons form equally well in both cases (bright fibers in images B and D). Images A and B illustrate Schwann cells and axons of dorsal root ganglions of the same culture, which were encapsulated. Images C and D relate to the non-encapsulated culture. It was therefore shown that the permeability of the gelatin tubes was sufficient to enable survival of encapsulated cells.

The invention claimed is:

1. A nerve guide comprising a shaped hollow body in the form of a tubule having a wall with an external surface and an internal surface which defines a lumen, wherein the shaped body comprises a cross-linked, resorbable material comprising gelatin, the nerve guide comprising a semipermeable layer surrounding the lumen, wherein
   (a) the semipermeable layer has a gel structure functioning as a cell barrier;
   (b) the semipermeable layer has pores which are on average less than 0.5 µm;
   (c) the semipermeable layer is a barrier layer for positively charged species;
   (d) the semipermeable layer is hydrophilic; or
   (e) the semipermeable layer comprises gelatin modified with esters of fatty acids.

2. The nerve guide according to claim 1, wherein the gel structure is produced from a further material comprising gelatin.

3. The nerve guide according to claim 1, wherein the gelatin modified with esters of fatty acids is modified with esters of fatty acids at the amino groups of 10 to 80% of the lysine groups.

4. The nerve guide according to claim 1, wherein the nerve guide or its shaped body has immobilised repulsion proteins on the external surface.

5. The nerve guide according claim 1, wherein the nerve guide comprises a reinforcing material.

6. The nerve guide according to claim 5, wherein the reinforcing material in the nerve guide has a fraction of dry mass of 5% by weight or more.

7. The nerve guide according to claim 5, wherein the reinforcing material has a fraction of dry mass of the nerve guide of up to 60% by weight.

8. The nerve guide according to claim 5, wherein the reinforcing material is selected from particulate and/or molecular reinforcing materials.

9. The nerve guide according to claim 8, wherein the particulate reinforcing material comprises reinforcing fibers.

10. The nerve guide according to claim 9, wherein the reinforcing fibers are selected from polysaccharide fibers and protein fibers, as well as polyactide fibers and mixtures of any of the foregoing.

11. The nerve guide according to claim 8, wherein the molecular reinforcing material is selected from polyactide polymers and their derivatives, cellulose derivatives, and chitosan and its derivatives.

12. The nerve guide according to claim 1, wherein the shaped body comprises a plurality of layers.

13. The nerve guide according to claim 1, wherein the material consists entirely of gelatin.

14. The nerve guide according to claim 1, wherein the material comprises gelatin of high molecular weight.

15. The nerve guide according to claim 1, wherein the gelatin has an endotoxin content, as determined by the limulus amebocyte lysate (LAL) test, of 1,200 I.U./g or less.

16. The nerve guide according to claim 1, wherein the material of the shaped body further comprises a plasticizer.

17. The nerve guide according to claim 1, wherein the shaped body is stretched in the direction of its longitudinal axis.

18. The nerve guide according to claim 17, wherein the stretch ratio is 1.4 to 8.

19. The nerve guide according to claim 1, wherein the nerve guide has an ultimate elongation in its longitudinal direction of 30% or more.

20. The nerve guide according to claim 1, wherein the nerve guide has a tear strength in the longitudinal direction of 40 N/mm$^2$ or more.

21. The nerve guide according to claim 1, wherein the degree of cross-linking of the material comprising gelatin in the wall of the shaped body neighboring the external surface is higher than in the regions of the wall neighboring the internal surface.

22. The nerve guide according to claim 1, wherein the nerve guide comprises one or more guide elements which are aligned in the longitudinal direction in the lumen of the shaped body.

23. The nerve guide according to claim 22, wherein the nerve guide comprises auxiliary cells which are populated on the guide elements.

24. The nerve guide according to claim 22, wherein the guide elements occupy up to 30% by volume of the lumen.

25. The nerve guide according to claim 22, wherein the guide elements comprise microfilaments.

26. The nerve guide according to claim 25, wherein the microfilaments have an average thickness from 10 µm to 100 µm.

27. The nerve guide according to claim 25, wherein the microfilaments have longitudinal grooves on their external surface.

28. The nerve guide according to claim 25, wherein the microfilaments in the lumen of the shaped body are held in a substantially uniformly distributed manner, as seen over the cross-section, by means of a matrix of a resorbable material.

29. The nerve guide according to claim 28, wherein the matrix is formed from a hydrophobic material comprising gelatin.

30. The nerve guide according to claim 22, the one or more guide elements being a roll of planar material which has an axis of rolling extending parallel to the longitudinal direction of the shaped body, thereby forming a plurality of microchannels in the roll, parallel to the axis of rolling.

31. The nerve guide according to claim 1, wherein the nerve guide comprises a plurality of shaped hollow bodies in parallel disposition.

32. The nerve guide according to claim 31, wherein the plurality of shaped bodies are bonded to one another by means of a resorbable matrix material.

33. The nerve guide according to claim 32, wherein the matrix material has an open-pored structure.

34. The nerve guide according to 1, wherein the nerve guide comprises a resorbable outer sleeve surrounding the shaped body.

35. The nerve guide according to claim 34, wherein the outer sleeve comprises an angiogenesis-promoting constituent.

36. The nerve guide according to claim 35, wherein the angiogenesis-promoting constituent comprises a gelatin of high molecular weight.

37. The nerve guide according to claim 34, wherein the outer sleeve has an open-pored structure.

38. The nerve guide according to claim 34, wherein the outer sleeve has, under standard physiological conditions, a higher rate of resorption than that of the shaped body.

39. The nerve guide according to claim 1, wherein the degree of cross-linking of the nerve guide or its shaped body is higher at one end of the nerve guide than that at the other end and reduces in a plurality of steps or continuously in the direction of the other end.

40. The nerve guide according to claim 1, wherein the degree of cross-linking of the nerve guide or its shaped body is less at its ends than it is in the region between the ends.

41. The nerve guide according to claim 1, wherein the diameter of the lumen at the two ends of the shaped body is greater than in the region of the shaped body between its ends.

42. The nerve guide according to claim 1, having a length in the range from 0.5 to 50 cm.

43. The nerve guide according to claim 1, having an internal diameter of about 1-30 mm.

44. The nerve guide according to claim 15, wherein the gelatin has an endotoxin content, as determined by the LAL test, of 200 I.U./g or less.

* * * * *